(12) United States Patent
Lee et al.

(10) Patent No.: US 7,982,870 B2
(45) Date of Patent: Jul. 19, 2011

(54) SURFACE ENHANCED RAMAN SCATTERING NANO-TAGGING PARTICLE AND METHOD FOR PREPARING THEREOF

(75) Inventors: Yoon-Sik Lee, Gyeonggi-do (KR); Dae-Hong Jeong, Seoul (KR); Jong-Ho Kim, Seoul (KR); Hee-Jeong Choi, Seoul (KR); Sang-Myung Lee, Gyeongbuk (KR)

(73) Assignee: Seoul National University Industry Foundation, Seoul (KR)

( * ) Notice: Subject to any disclaimer, the term of this patent is extended or adjusted under 35 U.S.C. 154(b) by 331 days.

(21) Appl. No.: 12/308,505

(22) PCT Filed: Sep. 29, 2006

(86) PCT No.: PCT/KR2006/003944
§ 371 (c)(1),
(2), (4) Date: Dec. 15, 2008

(87) PCT Pub. No.: WO2008/001978
PCT Pub. Date: Jan. 3, 2008

(65) Prior Publication Data
US 2010/0321683 A1    Dec. 23, 2010

(30) Foreign Application Priority Data
Jun. 28, 2006 (KR) .................. 10-2006-0058841

(51) Int. Cl.
*G01J 3/44* (2006.01)
*G01N 21/65* (2006.01)

(52) U.S. Cl. ...................................... 356/301
(58) Field of Classification Search ........... 356/301
See application file for complete search history.

(56) References Cited

U.S. PATENT DOCUMENTS

| | | | |
|---|---|---|---|
| 6,219,137 B1 | 4/2001 | Vo-Dinh | |
| 6,242,264 B1 | 6/2001 | Natan et al. | |
| 6,514,767 B1 | 2/2003 | Natan | |
| 6,685,986 B2 | 2/2004 | Oldenburg et al. | |
| 2002/0160195 A1* | 10/2002 | Halas et al. ............... | 428/403 |

OTHER PUBLICATIONS

PCT Application No. PCT/KR2006/003944, Search Report, Mailed Mar. 21, 2007.
Werner Stober et al., "Controlled Growth of Monodisperse Silica Spheres in the Micron Size Range", Journal of Colloid and Interface Science 26, pp. 62-69, 1968.
Thierry Cassagneau et al., "Contiguous Silver Nanoparticle Coatings on Dielectric Spheres", Advanced Materials, vol. 14, No. 10, pp. 732-736, May 17, 2002.

* cited by examiner

*Primary Examiner* — F. L Evans
(74) *Attorney, Agent, or Firm* — Meyertons, Hood, Kivlin, Kowert & Goetzel, P.C.; Eric B. Meyertons

(57) ABSTRACT

There is provided a method for manufacturing a surface enhanced Raman scattering nano-tagging particle, the method including the steps of: introducing silver nanoparticles on the surface of a silica core particle; immobilizing tagging materials and silica shell precursors on the silver nanoparticles; and forming a silica shell surrounding the silica core particle to which the tagging materials and the silica shell precursor are immobilized.

10 Claims, 9 Drawing Sheets

SURFACE ENHANCED RAMAN SCATTERING NANO-TAGGING PARTICLE AND METHOD FOR PREPARING THEREOF

TECHNICAL FIELD

The present invention relates to a surface enhanced Raman scattering nano-tagging particles and a method for fabricating the same; and, more particularly, to a surface enhanced Raman scattering nano-tagging particles capable of being used for detecting biomolecules in a high speed and a method for fabricating the same.

BACKGROUND ART

During the past several years, the nanoparticle and the chemical substance tagged by a special material have been widely used to conduct the researches in the metabolism, distribution and bind, etc., of a biomolecule and small amount of synthetic material in the biochemistry field. Remarkably, there are several methods for using the radioactive isotope, the organic phosphor and the inorganic quantum dot (Qdots).

In the method using the radioactive isotopes, $^3H$, $^{14}C$, $^{32}P$, $^{35}S$, $^{125}I$, and the like, which are the radioisotopes of $^1H$, $^{12}C$, $^{31}P$, $^{32}S$, $^{127}I$ and the like which are generally discovered in an organism, are widely used. Since the chemical characteristics of the radioactive isotopes are almost the same as that of the non-radioactive isotopes, it is possible to make an arbitrary substitution and they have the advantages in that emitting energy is relatively high and then the detection can be made by a small amount thereof. Therefore, the radioactive isotopes have been used for a long time in the different fields. However, it is hard work to handle them in the human body because of the radiation. In addition, they have the disadvantage of being inconvenient in safekeeping with a person or the experiment for the long time because of a short half life even if the emitting energy is high.

Organic fluorescent dyes are widely used as an alternative of the radioactive isotopes. The organic fluorescent dyes radiate the light which has a specific wavelength when they are activated by a specific wave. Particularly, as a detecting method is carried out in a miniaturized apparatus, the detection of the radioactive substance is limited in an amount and the long time is required for the detection. Meanwhile, in case of the organic fluorescent dyes which can emit a few thousand photons per molecule in an appropriate condition, it is possible to detect a few photons on a mono-molecular level, theoretically. However, being different from the radioactive isotopes, the organic fluorescent dyes have limitations in that it is not possible to directly substitute an element of the active ligand with others and a part, which does not relatively affect the activity, has to be connected to the organic fluorescent dyes through the structure-activity relation. Moreover, the organic fluorescent dyes have disadvantages in that the fluorescence intensity of these fluorescent marker materials is gradually weak (photobleaching) as time goes on and an interference between the different fluorescent materials is generated because the wavelength of the emitted light is very broad. Further, the fluorescent materials to be used are exceedingly limited in numbers.

On the other hand, a quantum dot, which is the semiconductor nanostructure, is composed of CdSe, CdS, ZnS, ZnSe, etc., and these radiate different colors of the light according to the size and kind of the nanostructure. As compared with the organic fluorescent dyes, since the quantum dot has a broad activating wavelength and a narrow emitting wavelength, the number of colors of the light from the semiconductor nanostructure is lager than that from the organic fluorescent dyes. Therefore, recently, the quantum dot is very much used as a method for overcoming the disadvantages of the organic fluorescent dyes. However, it has strong toxicity and the mass production is hard. Further, the large number of kinds of the quantum dots can be used, theoretically; however, the quantum dots which are actually used are exceedingly limited in numbers.

To solve the problem, a tagging material using the surface enhanced Raman scattering method has been recently used. Typically, there is introduced a method for using 5 to 10 nm gold nanoparticles and DNA in order to make a surface enhanced Raman scattering tagging material. First, after introducing a thiol group having a strong affinity with the gold nanoparticles to the 3' ends of DNA, Cy3, Cy3.5, and Cy5 are respectively introduced as the tagging materials and a ligand capable of recognizing a specific biomass is introduced into the 5' end of DNA. The DNA which is modified as set forth above is introduced onto the gold nano surface and this is used as the tagging material. After this surface enhanced Raman scattering gold nano-tagging particles reacts on a target biomass, they are analyzed after the strong Raman activity based on the silver ions. However, this method has the disadvantage in that it is hard to modify the DNA and the cost is high to reform DNA used as the tagging material.

DISCLOSURE

Technical Problem

An embodiment of the present invention is directed to providing a tagging nanoparticle which is capable of effectively and economically detecting biomolecules in a high speed.

Other objects and advantages of the present invention can be understood by the following description, and become apparent with reference to the embodiments of the present invention. Also, it is obvious to those skilled in the art of the present invention that the objects and advantages of the present invention can be realized by the means as claimed and combinations thereof.

Technical Solution

In accordance with an aspect of the present invention, there is provided a surface enhanced Raman scattering nano-tagging particle including: a silica core particle onto which silver nanoparticles are introduced, wherein tagging materials and a silica shell precursor are immobilized on the surface of silver nanoparticles; and a silica shell surrounding the silica core particle.

In accordance with another aspect of the present invention, there is provided a method for manufacturing a surface enhanced Raman scattering nano-tagging particle, the method including the steps of: introducing silver nanoparticles on the surface of a silica core particle; immobilizing tagging materials and silica shell precursors on the silver nanoparticles; and forming a silica shell surrounding the silica core particle to which the tagging materials and the silica shell precursor are immobilized.

Advantageous Effects

Surface enhanced Raman scattering nano-tagging particles according to the present invention can be conveniently manufactured and analysis of the nano-tagging particles is facilitated because of their high sensitivity in Raman spectroscopy.

Moreover, since the various kinds of chemical substances can be used as Raman tagging materials, the surface enhanced Raman scattering nano-tagging particles according to the present invention can be very economically manufactured. Therefore, the surface enhanced Raman scattering nano-tagging particles according to the present invention can be effectively used to detect a large number of biomolecules quickly and sensitively.

BEST MODE FOR THE INVENTION

Figure 1:
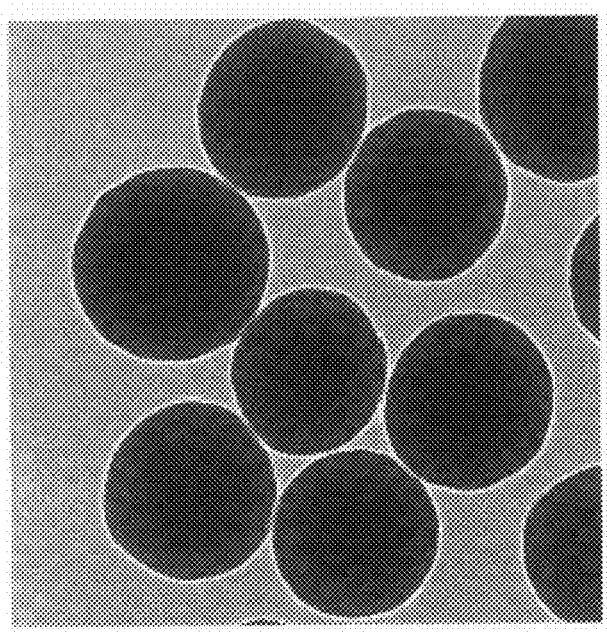
FIG. 1 is a TEM image of a silica core particle having a diameter in a range of 50 to 300 nm.

The advantages, features and aspects of the invention will become apparent from the following description of the embodiments with reference to the accompanying drawings, which is set forth hereinafter.

The surface enhanced Raman scattering nano-tagging particles according to the present invention are characterized in that they are made of 1) a silica core particle onto which silver nanoparticles are introduced and in which Raman tagging materials and a silica shell precursor are immobilized to the silver nanoparticles, and 2) a silica shell surrounding the silica core particle.

The silica core particle forming the surface enhanced Raman scattering nano-tagging particles according to the present invention preferably has the size of 50 to 300 nm. The surface-enhanced Raman scattering effect is degraded in the case where the silica core particle has the size of less than 50 nm and there is a problem in the biological application in the case where the silica core particle has the size of more than 300 nm.

First, the silver nanoparticles are introduced on the surface of silica core particles and the silver nanoparticles facilitate the analysis through the Raman spectroscopy by providing the enhanced Raman scattering effect on the silica core particles. That is, the silica core particle to which the silver nanoparticles are introduced has an advantage providing the very intense signals from any kinds of chemical substances because the surface enhanced scattering effect (surface enhanced Raman scattering) is very high.

Next, a specific Raman tagging material and the silica shell precursor are immobilized on the surface of silver nanoparticles which are embedded on the surface of silica core particles and the Raman tagging materials and the silica shell precursor are randomly immobilized at a ratio of 1:5 (molar ratio). All of the Raman tagging materials show their own specific Raman spectra without overlapping, which makes it easy and possible to analyze a large number of biomolecules at the same time.

The Raman tagging materials are chemical substances to have the affinity with silver nanoparticles and can be preferably, but not limited to, one selected from the group consisting of 2-methylbenzenethiol, 4-methylbenzenethiol, 4-mercaptopyridine, 2-naphthalenethiol, 4-methoxybenzenethiol, 3-methoxybenzenethiol, 3,4-dimethylbenzenethiol, thiophenol and 3,5-dimethylbenzenethiol. In the above case, the chemical substances to have the affinity with silver nanoparticles means that there are the thiol group (—SH), the amine group (—NH2), and the cyanide group (—CN) or the azide group (—N3) in their ends. Since the chemical substances having the thiol group (—SH), the amine group (—NH2), and the cyanide group (—CN) or the azide group (—N3) have the strong affinity with silver nanoparticles, it is desirable that these chemical material are used in the present invention.

The silica shell precursor can be preferably selected from the group consisting of 3-mercaptopropyltrimethoxysilane and 3-aminopropyltriethoxysilane.

Moreover, in the surface enhanced Raman scattering nano-tagging particles according to the present invention, the silica shell formed on the silica core particle can be made of tetraethyl orthosilicate and sodium silicate and, preferably, the silica shell has the thickness in a range of 10 to 50 nm. There is a problem in that silver nanoparticles and the Raman tagging materials are not protected safely at the time of processing the surfaces if the thickness of the silica shell is less than 10 nm. Also, there is a problem in that the signal processing of the Raman tagging materials can be obstructed if the thickness of the silica shell is more than 50 nm. Therefore, the thickness of the silica shell has to be controlled in an appropriate range.

Meanwhile, a method for manufacturing the surface enhanced Raman scattering nano-tagging particles is provided in the present invention. The method according to the present invention includes the steps of introducing silver nanoparticles on the surface of silica core particles; immobilizing Raman tagging materials and silica shell precursors on silver nanoparticles; and forming a silica shell surrounding the silica core particle to which the Raman tagging materials and the silica shell precursor are immobilized.

In the preferable embodiment of the present invention, the introduction of silver particles on the surface of silica core particles can be performed by reacting the precursor of silver nanoparticles with the silica core particle under the presence of solvents at a temperature of 40 to 100° C. The precursor of silver nanoparticles can be selected from, but not limited to, the group consisting of $AgNO_3$ and $AgClO_4$. It is preferable that ethylene glycol and ammonia solution can be used as a solvent and a base, respectively. There may be a problem with silver nanoparticles in that it will take a lot of time to form them when the reaction temperature is less than 40° C. and also there may be a problem with silver nanoparticles in that they are unevenly formed when the reaction temperature is more than 100° C. Therefore, the reaction may be carried out at a temperature of 40 to 100° C. in the preferable embodiment. The reaction can be controlled for 10 to 24 hours based on the reaction temperature.

Moreover, the step of immobilizing Raman tagging materials and silica shell precursor on the surface of silver nanoparticles can be carried out by applying the silica core particle, the Raman tagging materials and the silica shell precursors, especially for one hour at a room temperature.

Also, in the above case, the silica shell can be formed by treating the silica core particle with tetraethylortho silicate (TEOS) and sodium silicate, especially for 48 hours at a room temperature.

The size of the silica core particle and the silica shell, which are used in the method for manufacturing the surface enhanced Raman scattering nano-tagging particles according to the present invention, is the same as that mentioned above and the kind of the tagging materials and the silica shell precursors are also the same as that mentioned above.

Hereinafter, the embodiment according to the present invention will be described in detail.

However, the following embodiment exemplarily illustrates the present invention and the present invention is not restricted to the following embodiment.

Embodiment 1

Manufacture of the Surface Enhanced Raman Scattering Nano-Tagging Particles 1-1. Silica Core Particle Synthesis First, after reacting tetraethyl orthosilicate (1.6 g) with a mixed solution of ethanol (40 ml) and ammonia (3 ml) for 12 hours, the silica core particle of which the size is 50 to 300 nm is compounded through hydrolysis and concentration processes (*J. Colloid Interface Sci.* 1968, 26, 62) (FIG. 1). The silver nanoparticles are introduced on the surface of the silica core particle by reacting the precursor of silver particles, 30 mM $AgNO_3$ (3 ml) and ethylene glycol (3 ml) and ammonia (50 µl), with the silica core particle for 10 hours at a temperature of 50° C. (FIGS. 2 and 3).

Figure 2:
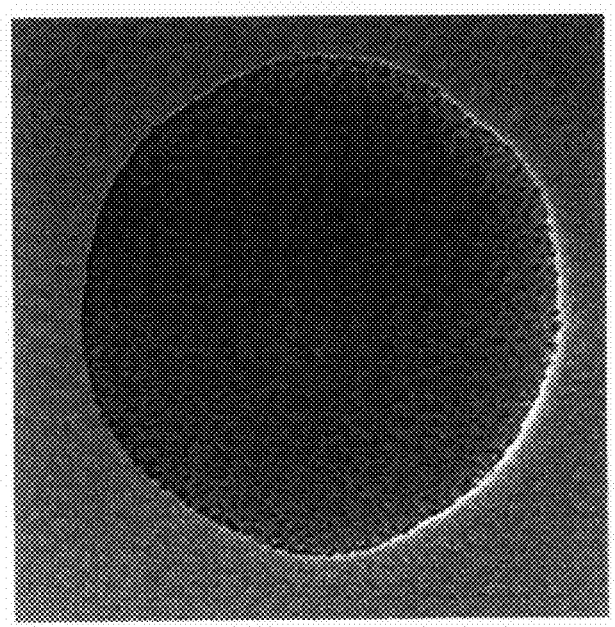
FIGS. 2 and 3 are TEM images of the silica core particle to which silver nanoparticles are introduced.
Figure 3:
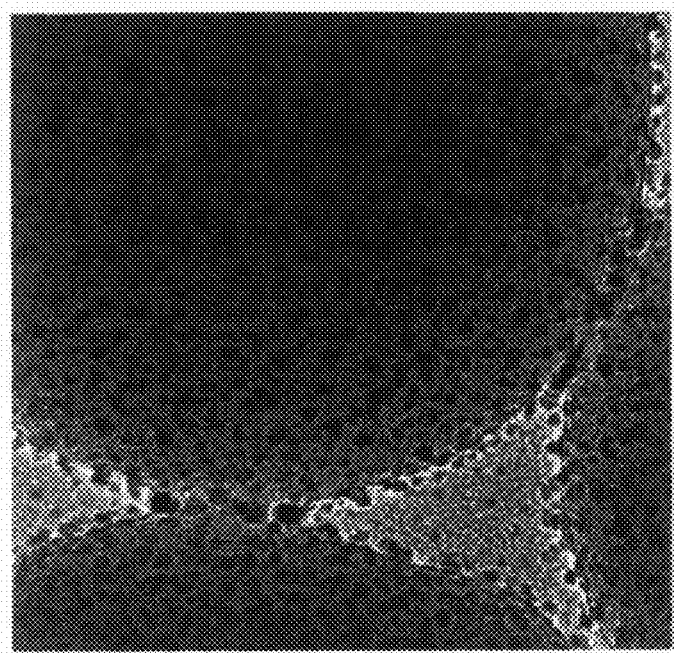
Figure 4:
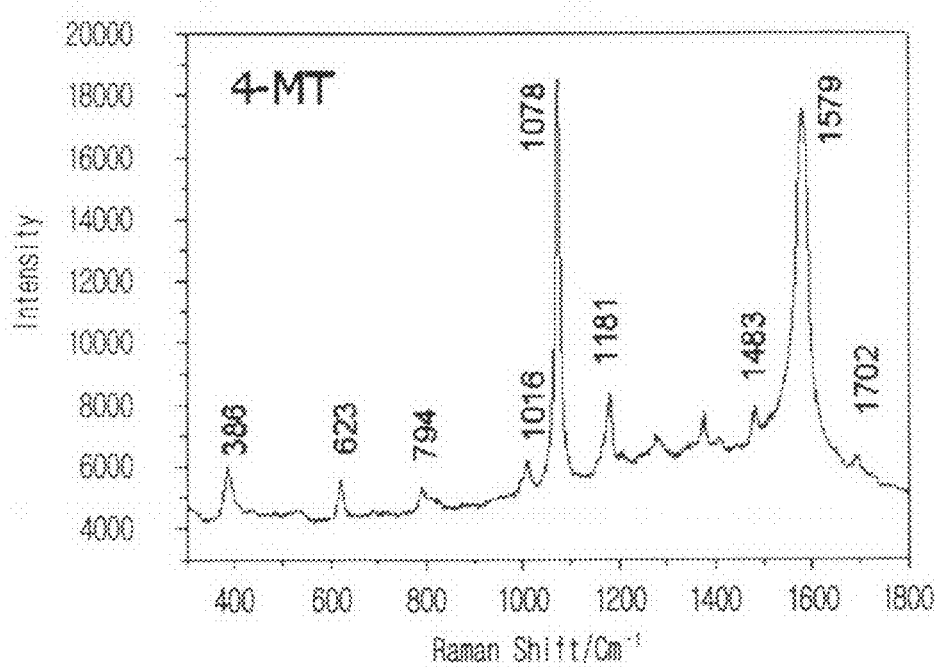
FIG. 4 is a graph showing a Raman spectrum analysis result after immobilizing 4-methylbenzenethiol on the surface of silver nanoparticles embedded on silica core particle in FIGS. 2 and 3.

In order to confirm that the synthesized silica core particles can be used appropriately as a template for a surface enhanced Raman scattering nano-tagging particle, an analysis is performed after introducing 4-methylbenzenethiol, as a tagging material, on the surface of silver nanoparticles embedded on the silica core particles, FIGS. 2 and 3, and the result are shown in FIG. 4.

As shown in FIG. 4, it can be confirmed that the surface enhanced Raman scattering effect on each particle is high. That is, as described above, it can be confirmed that the silver nanoparticle-embedded silica core particles can be appropriately used as the template for the surface enhanced Raman scattering nano-tagging particle.

1-2. Formation of Silica Shell

Figure 5:
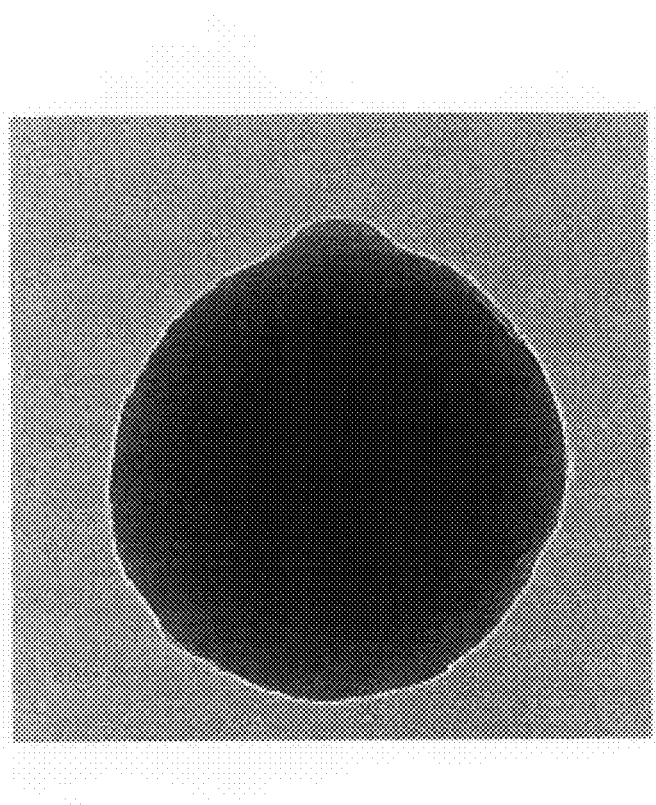
FIG. 5 is a TEM image of the surface enhanced Raman scattering nano-tagging particles according to the present invention in which 4-methylbenzenethiol is immobilized as a Raman tagging material.

After self-assembling both 4-methylbenzenethiol as the Raman tagging material and 3-mercaptopropyltrimethoxysilane as the precursor of the silica shell on the surface of silver nanoparticles embedded on the silica core particle for one hour at a room temperature, the self-assembled silica core particles were treated with tetraethyl orthosilicate and sodium silicate for 48 hours so that the silica shell having the thickness of about 15 nm is formed, thereby forming the surface enhanced scattering nano-tagging particles. The photograph of the manufactured surface enhanced Raman scattering nano-tagging particle is shown in FIG. 5.

Figure 6:
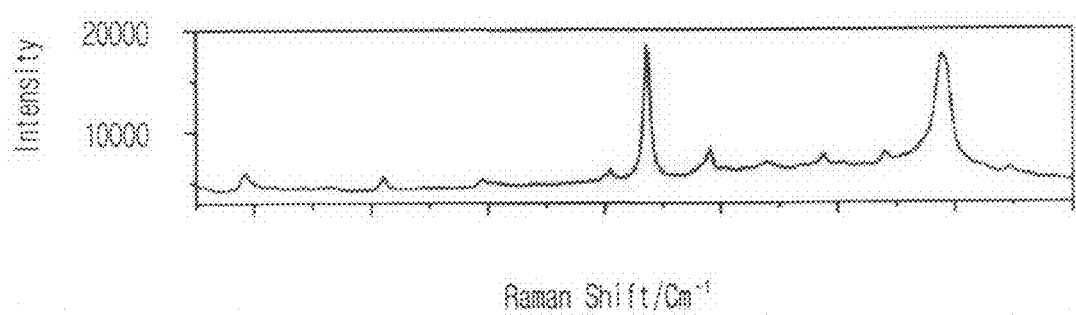
FIG. 6 is a graph showing a Raman spectrum analysis result of the surface enhanced Raman scattering nano-tagging particles according to the present invention in which 4-methylbenzenethiol is immobilized as a Raman tagging material.

The Raman analysis for the manufactured surface enhanced Raman scattering nano-tagging particle is performed and the result is in FIG. 6.

Referring to FIG. 6, it should be noted that the surface enhanced Raman scattering nano-tagging particle manufactured in the present invention maintains a characteristic of the Raman spectrum of the 4-methylbenzenethiol used as the Raman tagging material. That is, it can be confirmed that the particle manufactured in the present invention can be readily analyzed by the surface enhanced Raman scattering method.

Figure 7:
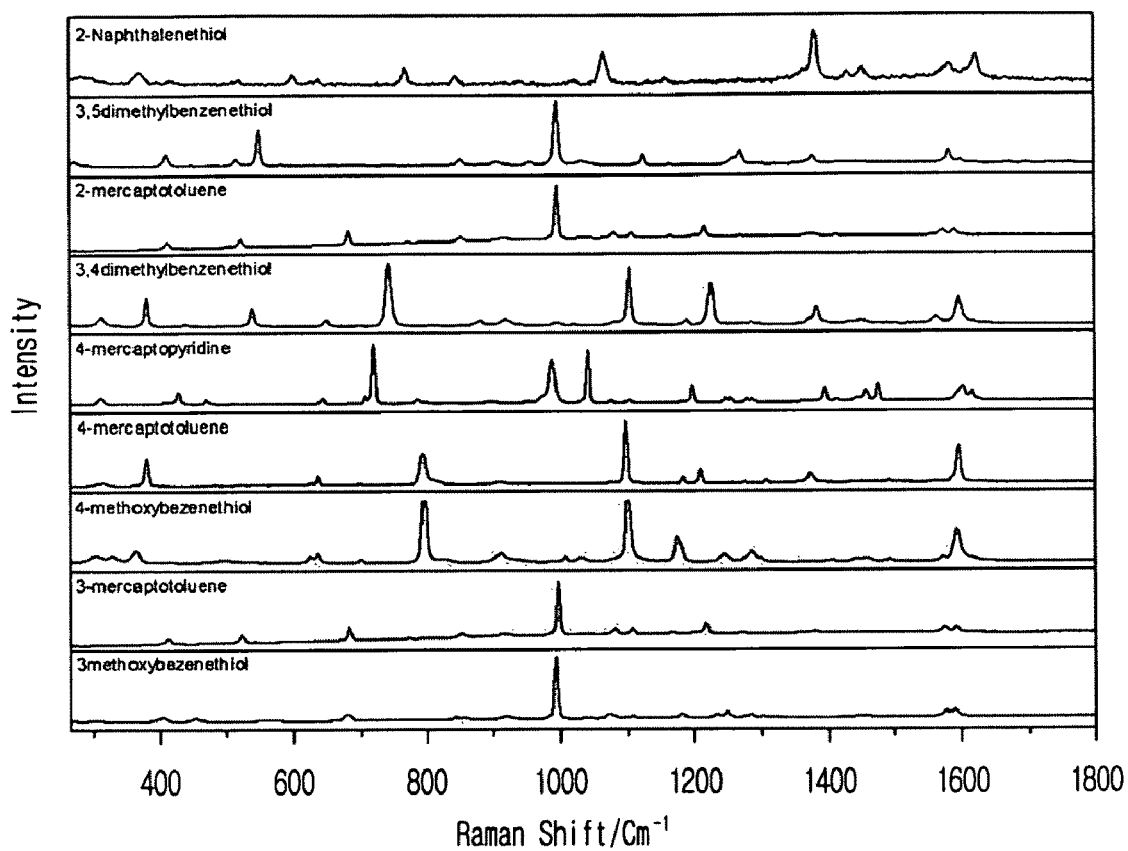
FIG. 7 is a graph showing Raman spectrum analysis results for the surface enhanced Raman scattering nano-tagging particles containing the different kinds of Raman tagging materials according to the present invention.

Meanwhile, the results of the Raman spectrum are shown in FIG. 7 based on the different kinds of tagging materials.

Embodiment 2

Experiment in Possibility of Biomolecule Detection with Surface Enhanced Raman Scattering Nano-Tagging Particle 2-1. Experiment of Introducing Nano-Tagging Particle into a Cell In order to confirm the bio-applicability of the surface enhanced Raman scattering nano-tagging particle manufactured in the above-motioned embodiment 1, the Raman analysis is performed after treating the nano-tagging particles in a cell and the results are shown in FIGS. 8 and 9.

Figure 8:
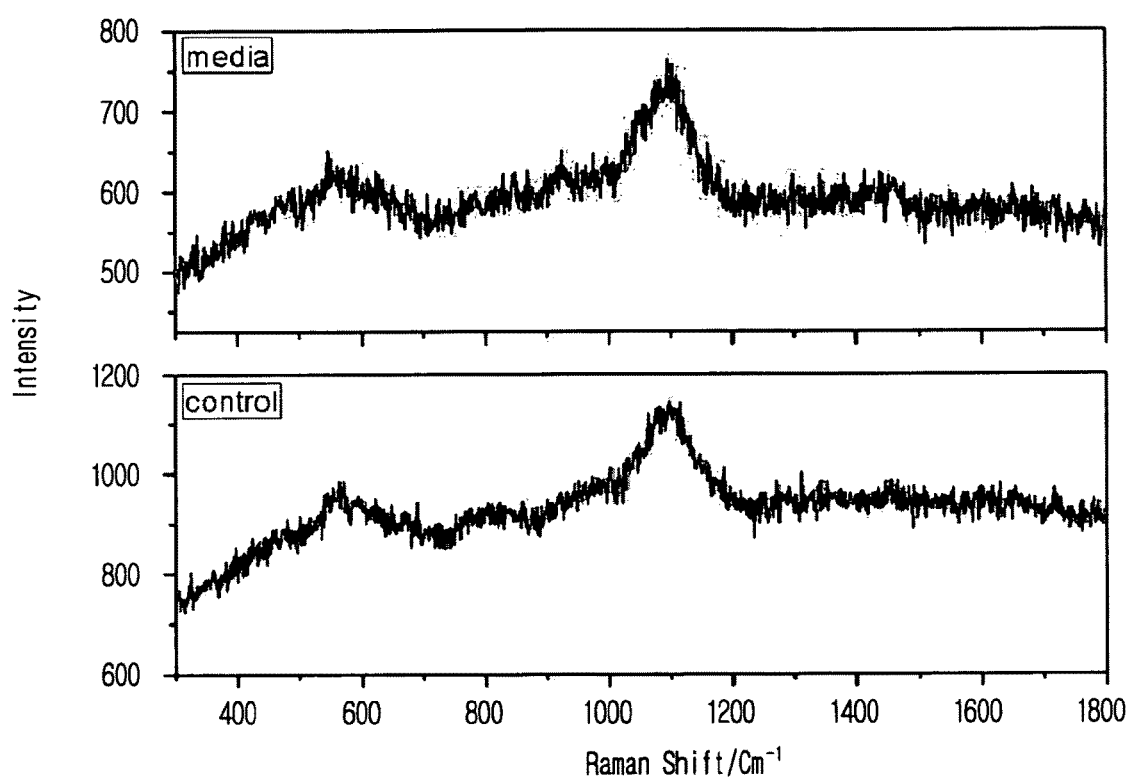
FIG. 8 is a graph showing a Raman spectrum analysis result for a control cell that is not treated with the surface enhanced Raman scattering nano-tagging particles.

In FIG. 8, "A" denotes the Raman spectrum about a culture medium and "B" denotes the Raman spectrum about a control group. Also, in FIG. 9, "A" denotes the Raman spectrum about 4-methylbenzenethiol and "B" denotes the Raman spectrum about the cell into which the surface enhanced Raman scattering tagging particle is introduced.

Figure 9:
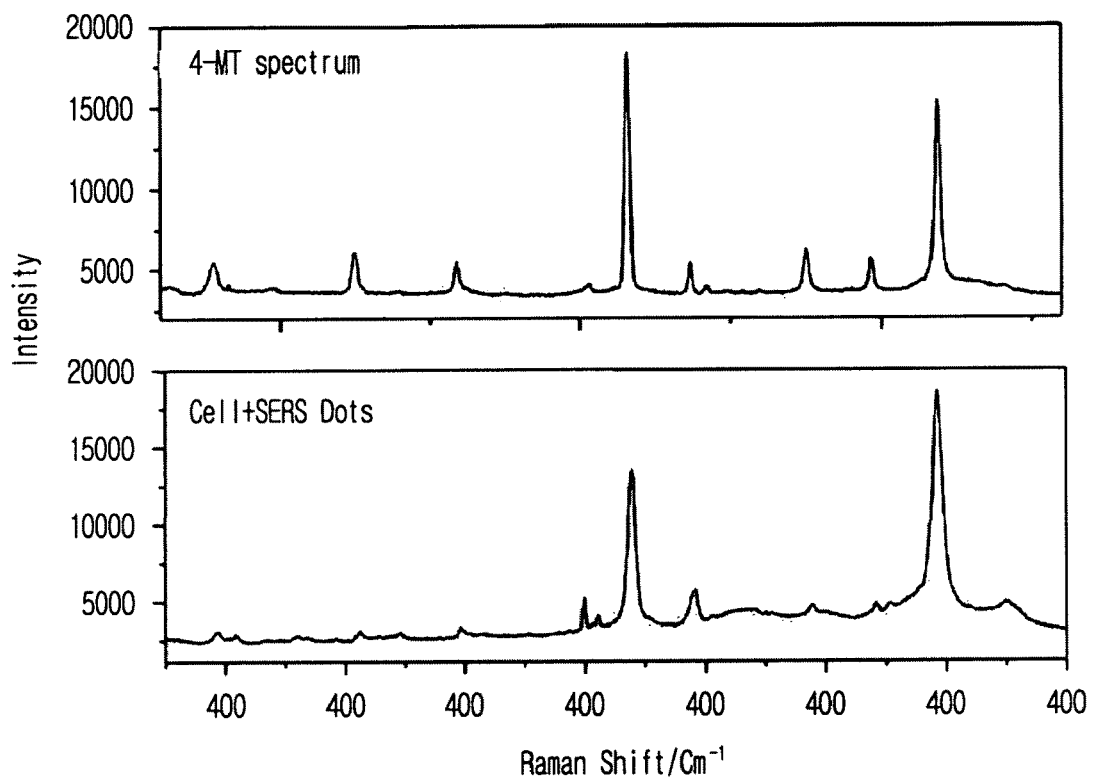
FIG. 9 is a graph showing a Raman spectrum analysis result for a cell that is treated with the surface enhanced Raman scattering nano-tagging particles according to the present invention are introduced.

As shown in FIGS. 8 and 9, the Raman spectrum of the tagging material does not show up in the control group to which the culture medium or the particle are not introduced, but the reproducibility clearly comes out in the cell to which the nano-tagging particle is introduced. That is, it should be noted that the particle manufactured in the present invention can be usefully used for the biomolecule detection.

2-2. Detection of Cancer Markers Existing on Cell Surface

The experiment of detecting the breast cancer marker HER2 and the leukemia marker CD10 existing on the cell surface is performed by using the surface enhanced Raman scattering nano-tagging particles manufactured according to the above-mention embodiment 1.

Figure 11:
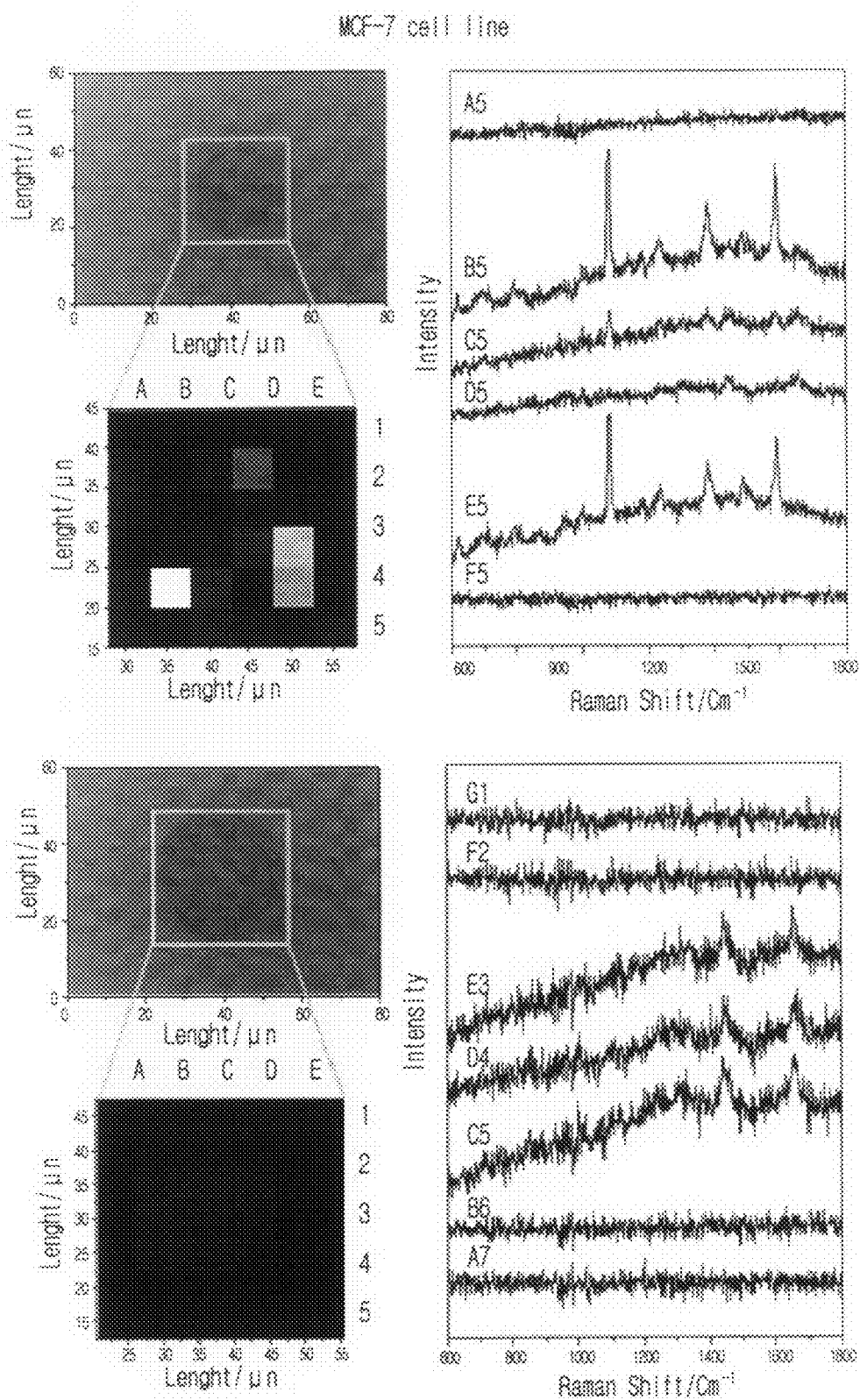
FIG. 11 is a spectrum showing an analysis result for a breast cancer cell, which has the biomarker HER2 on its surface, treated with the surface enhanced Raman scattering nano-tagging particle-HER2 antibody conjugate.

First, after introducing the anti-HER2 antibody to the surface enhanced Raman scattering nano-tagging particle tagged by 4-methylbenzenethiol (4-MT), reacting a breast cancer cell (MCF-7) having a HER2 breast cancer marker with the nano-tagging particle for 12 hours and cleaning the reactant, the Raman analysis is performed and the results are shown in FIG. 11. Further, after introducing the anti-CD10 antibody to the surface enhanced Raman scattering nano-tagging particle tagged by thiophenol (TP), reacting a leukemia cell (SP2/O) having a CD10 leukemia marker with the nano-tagging particle for 12 hours and cleaning the reactant, the Raman analysis is performed and the results are shown in FIG. 12.

Figure 10:
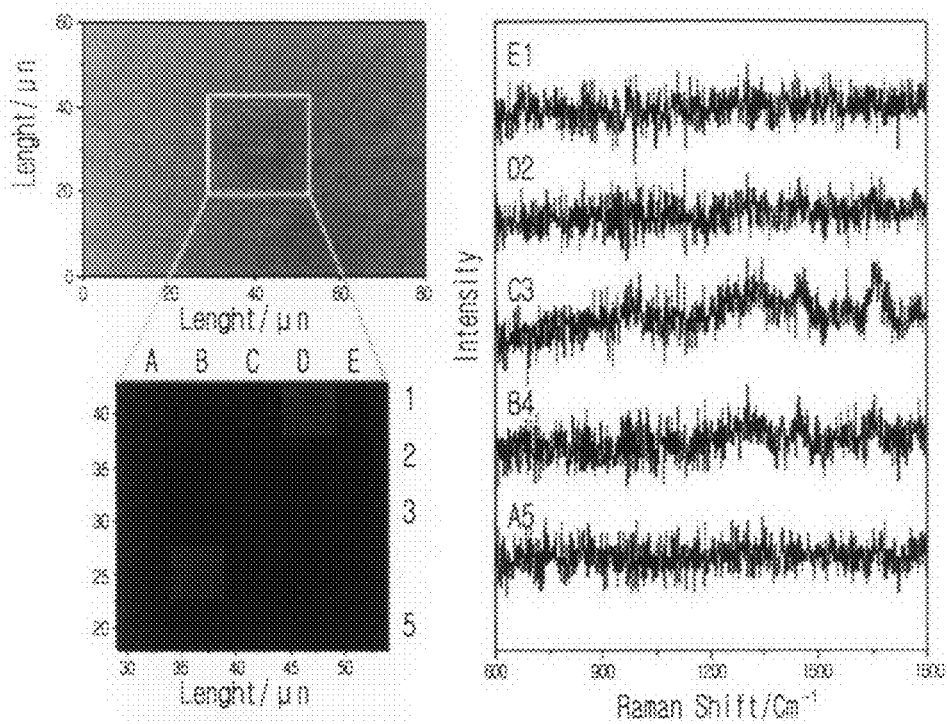
FIG. 10 is a spectrum showing an analysis result for a normal cell treated with the surface enhanced Raman scattering nano-tagging particle-antibody conjugates.
Figure 10:
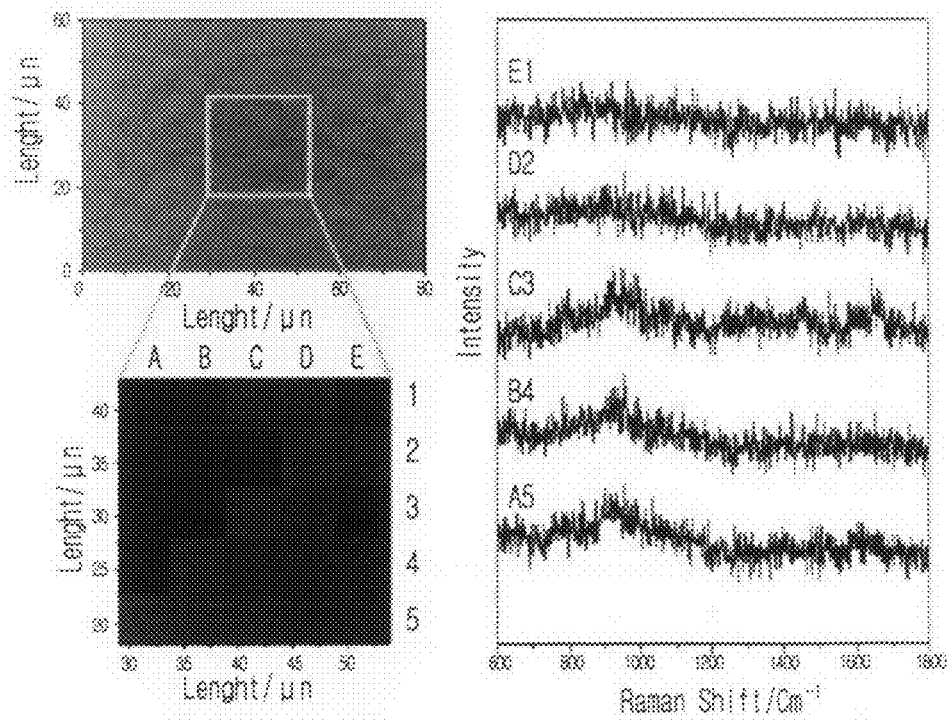
Figure 12:
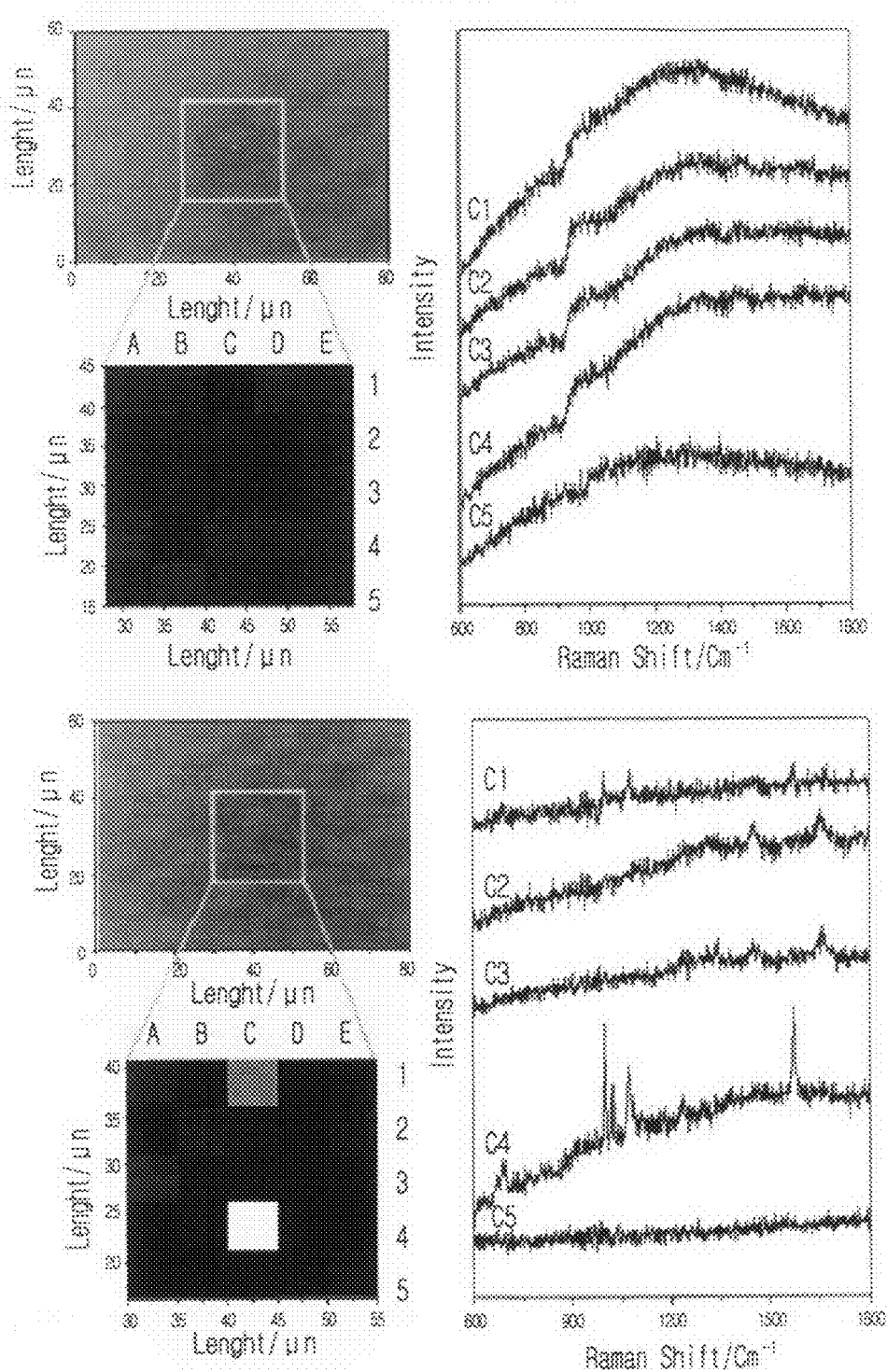
FIG. 12 is a spectrum showing an analysis result for a leukemia cell, which has the biomarker CD10 on its surface, treated with the surface enhanced Raman scattering nano-tagging particle-CD10 antibody conjugate.

As shown in FIG. 11, the surface enhanced Raman scattering nano-tagging particle having the anti-HER2 antibody is specifically bound to the breast cancer cell and, as shown in FIG. 12, the surface enhanced Raman scattering nano-tagging particle having the anti-CD10 antibody is specifically bound to the leukemia cell (SP2/O). However, any kinds of Raman spectra do not show up in the normal cell (NHBE) of the control group in FIG. 10.

That is, it can be confirmed that the surface enhanced Raman scattering nano-tagging particle manufactured in the present invention can be used in the diagnosis of a specific disease such as breast cancer or leukemia.

What is claimed is:

1. A surface enhanced Raman scattering nano-tagging particle comprising:
    a silica core particle onto which silver nanoparticles are introduced, wherein tagging materials and a silica shell precursor are immobilized on the surface of silver nanoparticles; and
    a silica shell surrounding the silica core particle.

2. The surface enhanced Raman scattering nano-tagging particle of claim 1, wherein the silica core particle has a particle size of approximately 50 to 300 nm.

3. The surface enhanced Raman scattering nano-tagging particle of claim 1, wherein the tagging materials are chemical substances to have a high affinity with the silver nanoparticles.

4. The surface enhanced Raman scattering nano-tagging particle of claim 3, wherein the tagging materials are one selected from the group consisting of 2-methylbenzenethiol, 4-methylbenzenethiol, 4-mercaptopyridine, 2-naphthalenethiol, 4-methoxybenzenethiol, 3-methoxybenzenethiol, 3,4-dimethylbenzenethiol, thiophenol and 3,5-dimethylbenzenethiol.

5. The surface enhanced Raman scattering nano-tagging particle of claim 1, wherein the silica shell precursor is one selected from the group consisting of 3-mercaptopropyl trimethoxysilane and 3-aminopropyltriethoxysilane.

6. The surface enhanced Raman scattering nano-tagging particle of claim 1, wherein the silica shell is made of tetraethyl orthosilicate and sodium silicate and wherein the silica shell has a thickness in a range of approximately 10 to 50 nm.

7. A method for manufacturing a surface enhanced Raman scattering nano-tagging particle, the method comprising the steps of:
    introducing silver nanoparticles on the surface of a silica core particle;
    immobilizing tagging materials and silica shell precursors on the silver nanoparticles; and
    forming a silica shell surrounding the silica core particle to which the tagging materials and the silica shell precursor are immobilized.

8. The method of claim 7, wherein the step of introducing silver nanoparticles is carried out by reacting the silica core particle with the silver nanoparticles at a temperature of approximately 40 to 100° C.

9. The method of claim 7, wherein the step of immobilizing tagging materials and silica shell precursors is carried out by applying the silica core particle, the tagging materials and the silica shell precursors for one hour at a room temperature.

10. The method of claim 7, wherein the step of forming the silica shell is carried out by reacting the silica core particle with tetraethylortho silicate (TEOS) and sodium silicate for 48 hours at a room temperature.

* * * * *